(12) United States Patent
Dryden

(10) Patent No.: US 10,792,058 B2
(45) Date of Patent: Oct. 6, 2020

(54) MEDICAL RETRIEVAL DEVICE

(71) Applicant: Gerald W. Dryden, Louisville, KY (US)

(72) Inventor: Gerald W. Dryden, Louisville, KY (US)

(*) Notice: Subject to any disclaimer, the term of this patent is extended or adjusted under 35 U.S.C. 154(b) by 122 days.

(21) Appl. No.: 15/966,833

(22) Filed: Apr. 30, 2018

(65) Prior Publication Data

US 2018/0242990 A1  Aug. 30, 2018

Related U.S. Application Data

(63) Continuation of application No. 14/712,394, filed on May 14, 2015, now Pat. No. 9,955,985.

(60) Provisional application No. 61/996,869, filed on May 14, 2014.

(51) Int. Cl.
| | |
|---|---|
| *A61B 17/221* | (2006.01) |
| *A61B 17/22* | (2006.01) |
| *A61B 17/50* | (2006.01) |
| *A61B 17/00* | (2006.01) |

(52) U.S. Cl.
CPC ...... *A61B 17/221* (2013.01); *A61B 17/00234* (2013.01); *A61B 17/22031* (2013.01); *A61B 17/50* (2013.01); *A61B 2017/00424* (2013.01); *A61B 2017/2212* (2013.01); *A61B 2017/2215* (2013.01); *A61B 2017/2217* (2013.01); *A61B 2017/22035* (2013.01)

(58) Field of Classification Search
CPC ............ A61B 17/00234; A61B 17/221; A61B 17/22031; A61B 17/50; A61B 2017/22035; A61B 2017/2212; A61B 2017/2215; A61B 2017/2217
See application file for complete search history.

(56) References Cited

U.S. PATENT DOCUMENTS

| | | | |
|---|---|---|---|
| 4,611,594 A * | 9/1986 | Grayhack | A61B 17/221 606/127 |
| 4,990,151 A | 2/1991 | Wallsten | |
| 5,374,273 A | 12/1994 | Nakao et al. | |
| 5,989,266 A | 11/1999 | Foster | |
| 6,093,196 A | 7/2000 | Okada | |

(Continued)

FOREIGN PATENT DOCUMENTS

| | | |
|---|---|---|
| WO | 9426179 | 11/1994 |
| WO | 2004082462 A2 | 9/2004 |
| WO | 2007110864 A2 | 10/2007 |

OTHER PUBLICATIONS

European Patent Office, Communication in Application No. 15726457.3 dated Sep. 17, 2019.

(Continued)

*Primary Examiner* — Robert A Lynch
(74) *Attorney, Agent, or Firm* — Middleton Reutlinger

(57) ABSTRACT

Apparatus and methods relating to a medical retrieval device that may include or be used with a catheter. A basket is included with an opening that is oriented transverse to the longitudinal direction in which the catheter extends. The basket may be extended and/or retracted relative to the catheter, and/or may be expanded and/or contracted to, for example, facilitate ensnaring and extraction of a foreign body, object, or polyp, etc. from a patient's esophagus, biliary tree, GI tract, urinary tract, abdominal cavity, kidney, bile duct, urethra, etc.

22 Claims, 4 Drawing Sheets

(56) References Cited

U.S. PATENT DOCUMENTS

| | | | |
|---|---|---|---|
| 6,152,932 | A | 11/2000 | Ternstrom |
| 6,171,315 | B1 | 1/2001 | Chu et al. |
| 6,216,044 | B1 | 4/2001 | Kordis |
| 6,270,505 | B1 | 8/2001 | Yoshida et al. |
| 6,383,195 | B1 | 5/2002 | Richard |
| 6,432,111 | B1 | 8/2002 | Ternstrom |
| 6,506,209 | B2 | 1/2003 | Ouchi |
| 6,802,846 | B2 | 10/2004 | Hauschild et al. |
| 6,971,988 | B2 | 12/2005 | Orban, III |
| 7,731,723 | B2 | 6/2010 | Kear et al. |
| 7,914,540 | B2 | 3/2011 | Schwartz et al. |
| 8,012,166 | B2 | 9/2011 | Rizvi |
| 8,016,771 | B2 | 9/2011 | Orban, III |
| 8,038,704 | B2 | 10/2011 | Sherburne |
| 8,172,772 | B2 | 5/2012 | Zwolinski et al. |
| 9,955,985 | B2 | 5/2018 | Dryden |
| 2006/0247662 | A1* | 11/2006 | Schwartz ............. A61B 17/221 606/114 |
| 2009/0222035 | A1 | 9/2009 | Schneiderman |
| 2010/0152609 | A1 | 6/2010 | Zwolinski |
| 2012/0029413 | A1 | 2/2012 | Meade et al. |
| 2015/0173783 | A1* | 6/2015 | Tah ...................... A61B 17/221 606/127 |

OTHER PUBLICATIONS

European Patent Office; Notification of Transmittal of the International Search Report and the Written Opinion of the International Searching Authority; dated Jul. 15, 2015, NL.
European Patent Office, Communication pursuant to Article 94(3) EPC for App. No. 15 726 457.3 dated Dec. 12, 2018.

* cited by examiner

MEDICAL RETRIEVAL DEVICE

CROSS-REFERENCE TO RELATED APPLICATIONS

This application claims priority to and benefit under 35 U.S.C. § 120 of U.S. Non-Provisional application Ser. No. 14/712,394 filed on May 14, 2015 entitled "Medical Retrieval Device", which claims priority to Provisional Application No. 61/996,869 filed on May 14, 2014 entitled "Medical Retrieval Device", the entire contents of both applications are herein incorporated by reference.

TECHNICAL FIELD

Generally, a medical device is taught. More particularly, a catheter type medical retrieval device for removing an object is taught.

BACKGROUND

It is often necessary to remove a foreign body or undesirable growth from a human patient. For example, a foreign body may become lodged in a patient's esophagus resulting in choking or asphyxiation. In another example, a polyp may grow in the patient's colon and need to be removed or resected. It is often desirable to access such foreign bodies, polyps, etc. through the body's natural passageways without the need for externally incising the patient. Thus, in order to access such objects, catheters have been used, which may enter, for example, the esophagus via the mouth without the need to incise the patient. Such catheters may also be used in the gastrointestinal tract, biliary tree, urinary tract, or abdominal cavity, etc.

Such catheters may include a retrieval device disposed at an end for use in removing or extracting a target object. However, such retrieval devices are typically oriented in line with the longitudinal axis of the catheter, which may be quite long, and thus are often oriented in line with the object that is to be removed. This can make it quite difficult to retrieve or extract the object with current devices such as nets and graspers, as much precision and skill may be required to engage the retrieval end of the device with the object. Such difficulty is often compounded by the length and flexibility of a retrieval catheter.

Thus, there is a need in the art for overcoming the issues of existing devices.

SUMMARY

The present disclosure is directed toward methods and apparatus for a medical retrieval device.

Generally, in one aspect, a medical retrieval device is provided having a handle coupled to a retrieval basket via an extension member and a constriction member. The extension member and the constriction member may engage one or more lumens of a catheter where the catheter and the lumen(s) extend away from the handle and toward the retrieval basket. The retrieval basket has a plurality of legs that extend away from the catheter in a longitudinal direction. Each leg has a proximal end attached to the extension member as well as a distal end extended away from the extension member in the longitudinal direction. The retrieval basket also has an open retrieval end defined by a basket rim that is engaged with the distal ends of the legs. The basket rim substantially defines a rim plane that is substantially transverse to the longitudinal direction in which the legs extend away from the catheter. The basket rim may be moved between an expanded rim position and a constricted rim position to, for example, expand for ensnaring a foreign body and constricted to tighten around the foreign body for removal. The extension member may move between an extended position and a retracted position to cause extension and retraction of the basket relative to the basket end of the catheter. The constriction member may move between a first position and a second position to cause the constriction and expansion of the basket rim.

Optionally, in some embodiments, a vacuum may be attached, connected, included with, and/or applied to one or more lumens of the catheter. In these embodiments or other embodiments, the vacuum may assist with removal of an object, polyp, and/or foreign body, for example, due at least in part to a suction force transferred through the catheter. In some embodiments, the medical retrieval device may include a basket sheath. A sheath, if included, may have an open end opposite a narrow end, and the narrow end may be connected to and/or located near the catheter. The open end of the sheath, if included, may be constrictable. Optionally, the extension member may be housed within a first lumen and/or the constriction member may be housed within a second lumen. The constriction member may engage each leg of the basket and thereby form the basket rim.

Generally, in another aspect, a retrieval basket for use with a medical catheter and having legs and basket rim is provided. The legs are in longitudinal translational communication with an extension member and the legs are also in radial translatable communication with the basket rim. Each leg has a proximal end and a distal end, with each proximal end connected to the extension member, which may slidably engage a catheter. Each distal end is extended longitudinally away from the proximal end of the leg it is on. The basket rim engages each distal end of the legs and the basket rim is in communication with a constriction member. Each distal end is biased radially outwardly from each proximal end to bias the basket rim toward an expanded position. Actuation of the constriction member causes constriction of the basket rim from the expanded position to a constricted position. The constriction of the basket rim is capable of overcoming the radial outward bias of the distal ends of the legs.

Optionally, in some embodiments, one or more of the legs may include a gripping member adjacent a distal end of the respective leg. One or more gripping members, if included, may include a finger or projection, which may extend inwardly toward the center of the basket to, for example, facilitate gripping of a foreign body, polyp, object, etc. In some embodiments, the legs may be substantially surrounded by a sheathing, covering, and/or netting member.

Generally, in another aspect, a medical retrieval device having a basket that may be actuated, as well as a handle and a constriction member, is provided. The actuatable basket is in communication with the constriction member and the handle, and the basket may be actuated between an expanded position and a constricted position. The basket projects outwardly from a catheter, which extends in a longitudinal direction away from the handle toward the basket. The basket has a basket rim that defines a basket opening and lies in a plane substantially transverse to the longitudinal direction. Actuation of the constriction member causes constriction of the basket rim from the expanded position to the constricted position. The handle is in communication with the constriction member. The handle also has a translatable constriction hold that may be actuated between and expanded hold position and a constriction hold position. Actuation of the translatable constriction hold causes actuation of the constriction member and constriction of the basket rim. Optionally, in some embodiments, the basket may be rotatable and/or rotation of the basket may be caused by rotation of the handle or a part of the handle such as a knob. The rotation may be communicated and/or transferred via the catheter, the extension member, and/or the constriction member causing the basket to rotate.

It should be appreciated that all combinations of the foregoing concepts and additional concepts discussed in greater detail below provided such concepts are not mutually inconsistent are contemplated as being part of the subject matter disclosed herein. In particular, all combinations of claimed subject matter appearing at the end of this disclosure are contemplated as being part of the subject matter disclosed herein.

BRIEF DESCRIPTION OF THE DRAWINGS

In the drawings, like reference characters generally refer to the same parts throughout the different views. Also, the drawings are not necessarily to scale, and emphasis instead is generally placed upon illustrating the principles of the embodiments depicted.

DETAILED DESCRIPTION

Figure 1:
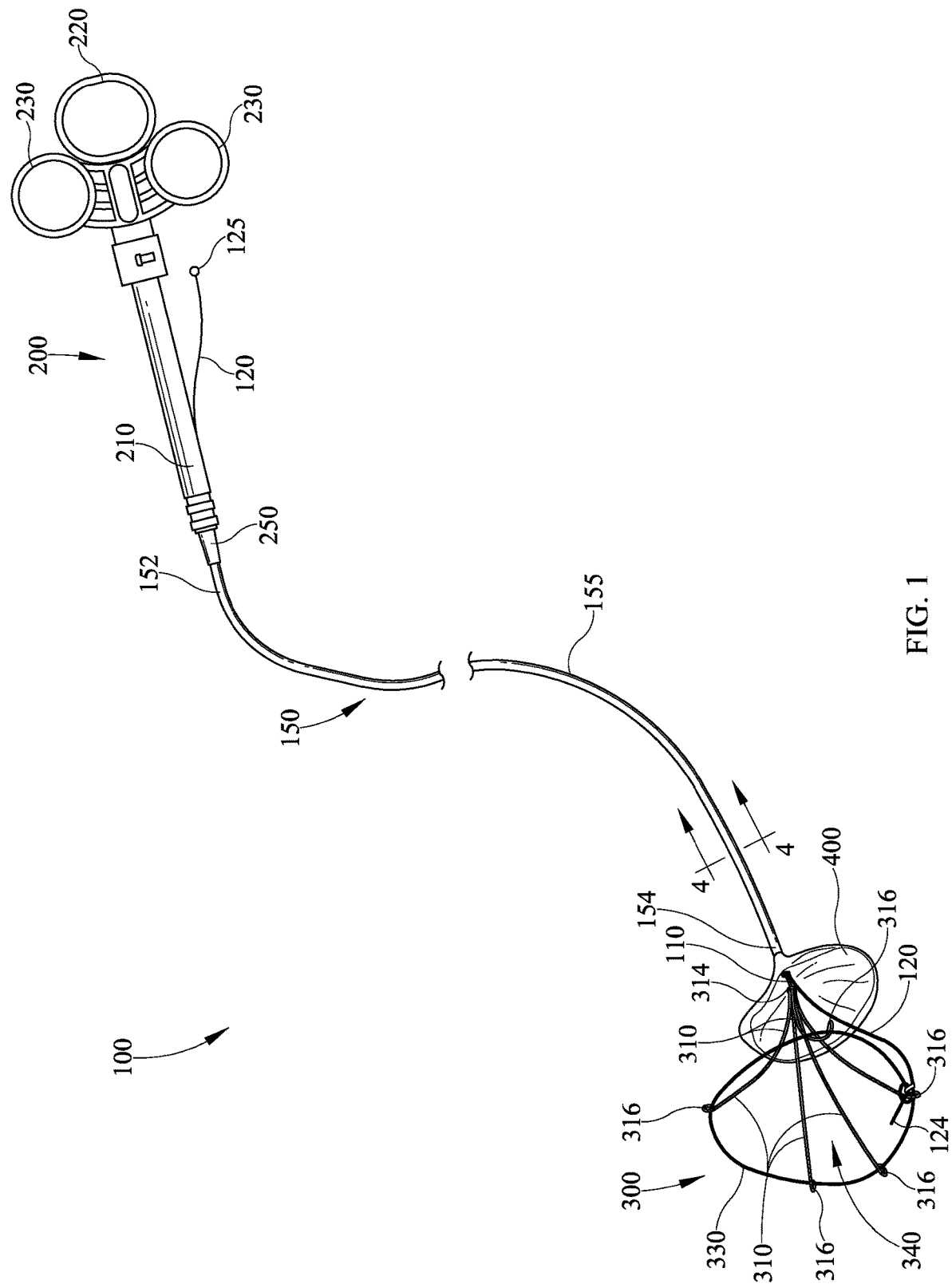
FIG. 1 is a perspective view of an embodiment of a medical retrieval device with a catheter of indeterminate length.

It is to be understood that the embodiments are not limited in their application to the details of construction and the arrangement of components set forth in the following description or illustrated in the drawings. Other embodiments are possible and may be practiced or carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless limited otherwise, the terms "connected" and "coupled" and variations thereof herein are used broadly and encompass direct and indirect connections and couplings. In addition, the terms "connected" and "coupled" and variations thereof are not restricted to physical or mechanical connections or couplings.

Figure 2:
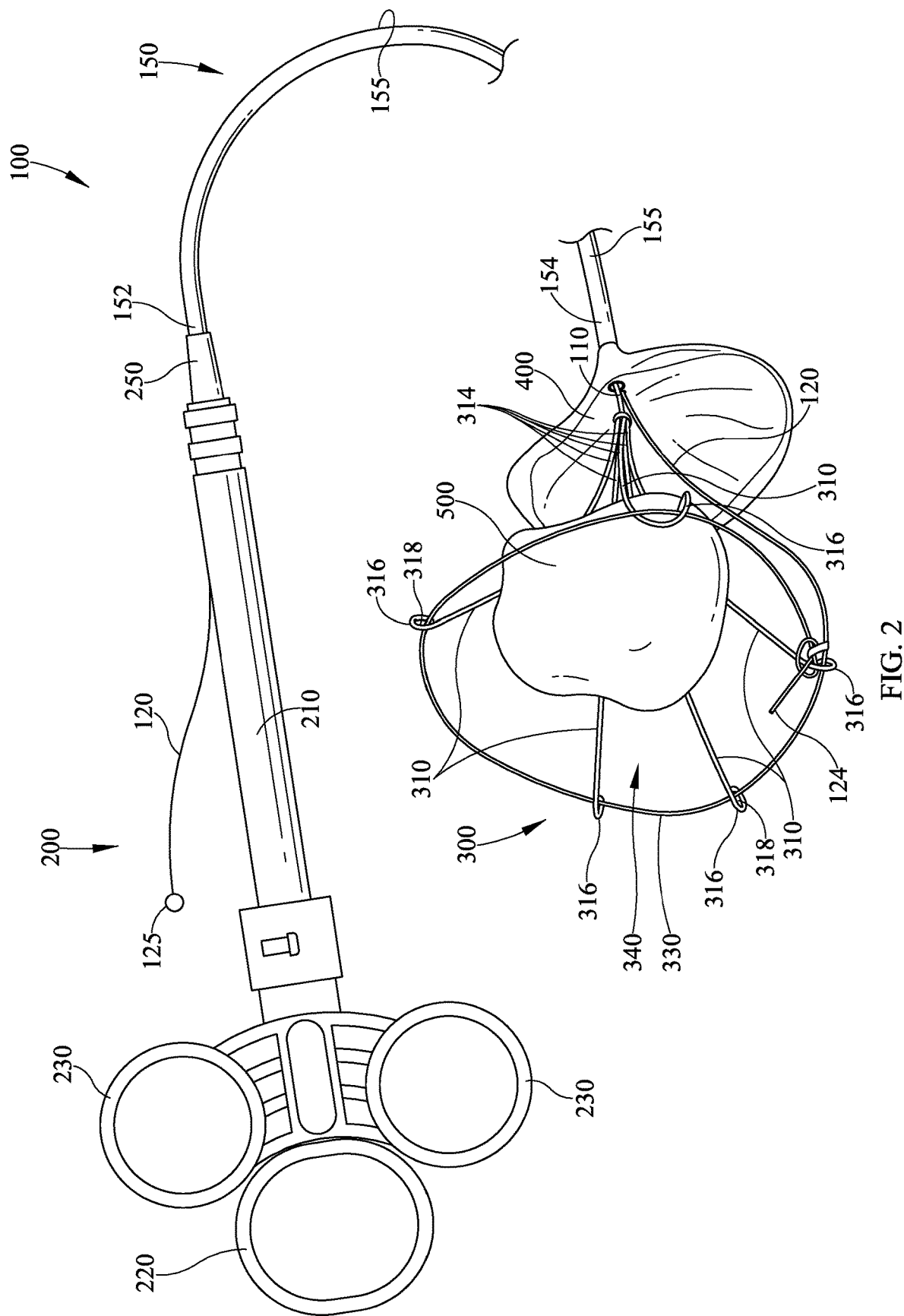
FIG. 2 is another perspective view of the medical retrieval device of FIG. 1 illustrated in an extended and expanded position.
Figure 3:
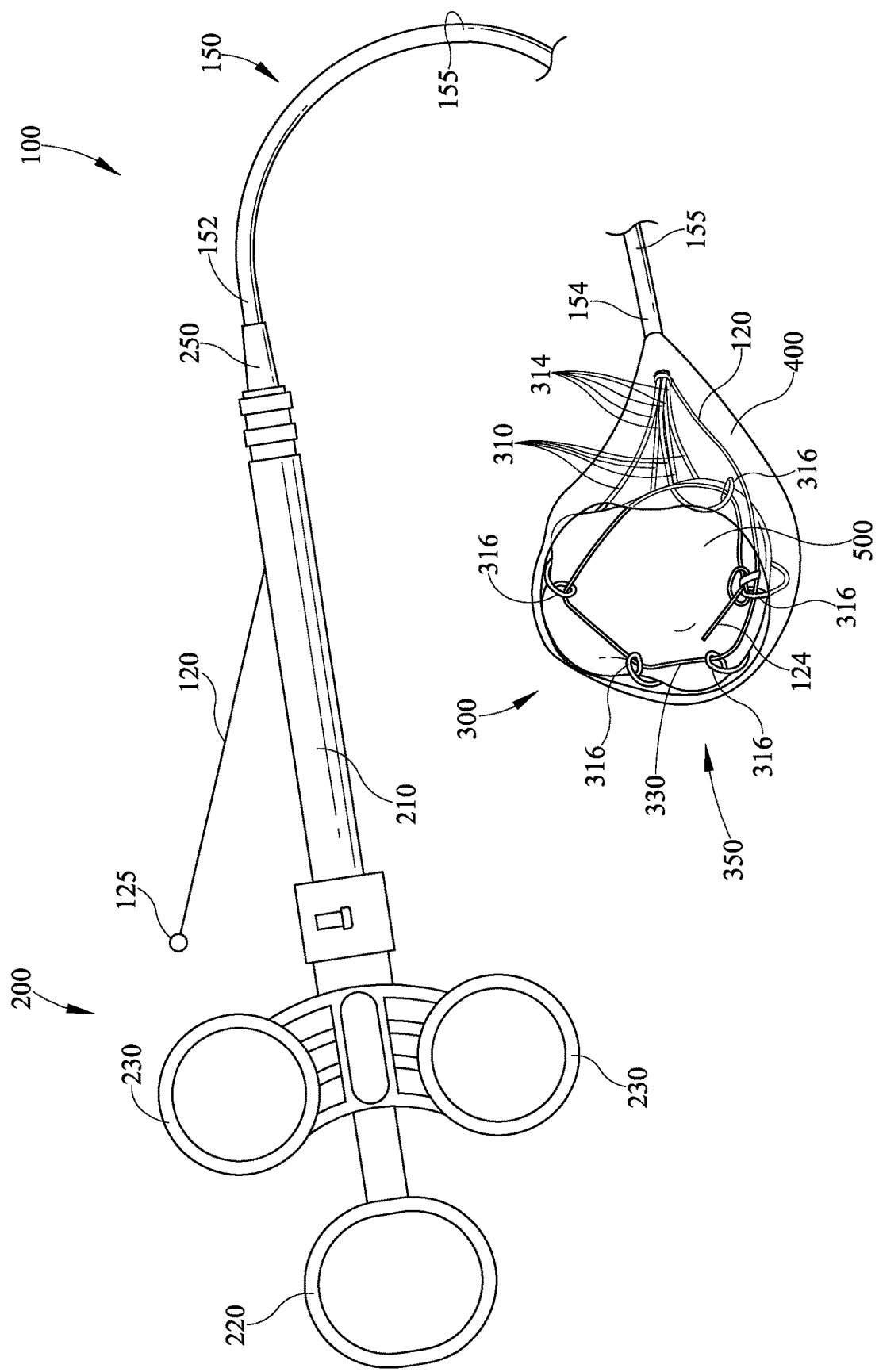
FIG. 3 is a perspective view of the medical retrieval device of FIG. 1 illustrated in a somewhat retracted and constricted position.

Referring initially to FIGS. 1-3, a medical retrieval device 100 is illustrated having a control mechanism or handle 200 connected to a catheter 150 (of indeterminate length), and a retrieval basket 300 also connected to catheter 150. Medical retrieval device 100, in the embodiment depicted, may be used with a catheter-based design suitable for endoscopic use, for example, by being insertable or suitable for placement through the working channel(s) of an endoscope. Retrieval basket 300 may be inserted into a body passageway, such as a throat or esophagus (and/or virtually anywhere in a patient's gastrointestinal (GI) tract, biliary tree, urinary tract, abdominal cavity, kidney, bile duct, urethra, etc.), facilitated by a relatively lengthy and/or flexible catheter 150. Handle 200 may remain outside of the body passageway of the patient so that it may be manipulated by, for example, an operating doctor or medical professional. Handle 200 may be in communication with retrieval basket 300 to cause extension, retraction, constriction, rotation and/or loosening of basket 300. Retrieval basket 300 may be inserted into the patient's body passageway, may follow the twists, turns, bends, angles, and/or contours of the passageway into which it is entered and remain in communication with handle 200, for example via catheter 150, and handle 200 may be used to cause extension, retraction, constriction, and/or loosening of retrieval basket 300. Medical retrieval device 100 may be used to access, approach, and/or engage an object or projection within a patient. For example, medical retrieval device 100 may be used to access, approach, engage, ensnare, and/or remove a foreign body 500 (e.g., a food morsel or a small item swallowed by a child) from a patient's esophagus. For another example, medical retrieval device 100 may be used to access, approach, engage, ensnare, and/or remove a stone or crystal from a bladder or gall bladder. For yet another example, medical retrieval device 100 may be used to access, approach, engage, ensnare, cut and/or shear, and/or remove a polyp (pedunculated, sessile, or otherwise) from a patient's colon. It is understood that these are merely examples and that medical retrieval device 100 may be used for any of a variety of purposes (or combination of purposes) and is not limited in use by these examples.

Retrieval basket 300 may be used to ensnare or grab such a foreign body 500, may be constricted around foreign body 500, and/or may be retracted into a sheath 400. If included, sheath 400 may be used to, for example, envelope foreign body 500 in retrieval basket 300 and/or to facilitate pulling foreign body and/or retrieval basket 300 through the patient and/or passageway. Sheath 400 may be attached to either or both of catheter 150 and retrieval basket 300 so that, for example, sheath 400 may be either static or dynamic relative to basket 300. In some embodiments, legs 310 may be connected with a mesh, netting, and/or solid covering, instead of or in addition to sheath 400, may be included to, for example, help prevent foreign body 500 from escaping between legs 310 and/or to reduce or eliminate trauma to the passageway during extraction.

Retrieval basket 300 may include one or more legs 310 that are connected to an extension member 110 that could be a tube, wire, or cable, either plastic or metallic. Extension member 110 may extend through catheter 150, into handle 200, and/or connect to a distal finger hold 220. Catheter 150 may have a handle end 152 that is connected to and/or adjacent a handle body 210 and/or a coupling 250. Catheter 150 may have a basket end 154 that is connected to and/or adjacent retrieval basket 300 and/or legs 310. In some embodiments, extension member 110 may extend through a hollow tube and/or a hypotube, which may extend from and/or be connected to catheter 150 at or near basket end 154. Such a hollow tube, or hypotube, if included, may facilitate conveying, supporting, and/or locating, for example, extension member 110, a constriction wire 120 (discussed below), suture, optical device, or any other feature or any combination thereof to or toward a distal end 316 of one or more legs 310. The hollow tube may be formed from a thermoplastic or metallic part. The tube may have one or multiple through holes/lumens. Distal finger hold 220 may slidably engage handle body 210 so that pulling distal finger hold 220 away from handle body 210 will cause extension member 110 to slide within catheter 150 and/or to pull and/or retract legs 310 and/or retrieval basket 300 toward basket end 154 of catheter 150 and/or toward (or into) a retracted position (see FIG. 3). Distal finger hold 220 may be pushed and/or moved toward handle body 210, which may cause extension member 110 to push and/or extend legs 310 and/or retrieval basket 300 away from basket end 154 of catheter 150 and/or toward (or into) an extended position (see FIG. 2). Handle 200 may include lateral finger holds 230, which may be rigidly affixed to handle body 210. An operator may insert a finger into one or both lateral finger holds 230 and cause relative motion of distal finger hold 220 with a third finger, for example. In this or any other way, cable or extension member 110, legs 310, and/or retrieval basket 300 may be moved or movable between an extended position and a retracted position. Moreover, in some embodiments, handle 200 and basket 300 may be coupled or connected so that extension member 110, constriction wire 120, and/or basket 300 may, for example, be rotated by corresponding rotation of handle 200 (or any component thereof). It is understood that extension member 110 and/or constriction wire 120 may have high torque carrying or transmitting properties or characteristics, although they are not required to have such properties.

Any or all of legs 310 may include a proximal end 314 that is connected to and/or adjacent extension member 110. Any or all of legs 310 may extend in a longitudinal direction away from catheter 150, and/or may include distal end 316 that is opposite proximal end 314. Legs 310 may be integral with and/or attach, connect, and/or be coupled to extension member 110, in any of a variety of ways, including, but not limited to, tying, looping, welding, mechanically fastening, sewing, suturing, adhering, gluing, bonding, or any other way or any combination thereof. A basket rim 330 may engage distal ends 316 and/or basket rim 330 may substantially define a rim plane that is substantially transverse to legs 310 and/or the longitudinal direction extending away from catheter 150 toward the rim plane. For example, basket rim 330 may be inserted and/or slid through one or more eyelets 318 formed in the distal ends 316.

In some embodiments one or more eyelets 318 and/or distal ends 316 may face the interior or center of basket 300 and/or may extend toward the interior or center of basket 300 so that they may, for example, facilitate grabbing of an object, foreign body, polyp, etc. In these or other embodiments, one or more eyelets 318 and/or distal ends 316 may include and/or have attached thereto one or more fingers or projections, for example, extending and/or pointing toward the center or interior of basket 300 so as to impale, penetrate, and/or apply gripping pressure to the object, foreign body, polyp, etc. Legs 310 may be formed substantially of hypotube or hollow tube, or flattened wire, for example, any or all of which may include a bumpout or the like that might facilitate threading constriction wire 120 through leg 310 and/or eyelet 318. Distal end 316 and/or eyelet 318 may be crimped, flattened, and/or turned toward the interior or center of basket 300 to act as a spike, finger, or projection to, for example, impale, penetrate, and/or apply pressure to the object, foreign body, polyp, etc.

In these or other embodiments, basket rim 330 may be formed integrally with and/or connected to constriction member or constriction wire 120, which may terminate and/or tie off to a distal end 316 of a leg 310, for example, at terminal end 124 of constriction wire 120. It is understood that, although extension member 110 is referred to as a cable and constriction member 120 is referred to as a wire herein, neither are limited to that description. For example, either or both of extension member 110 and constriction member 120 may be wire, cable, and/or any sufficiently resilient material that may be used for pushing without excessive buckling, and/or may include one or more metallic alloys (e.g., stainless steel or nickel titanium based alloys such as nitinol), braided suture, monofilament suture, or other suture, string, thread, yarn, rope, or any other material or type of material or any combination thereof, any or all of which may be substantially coated or uncoated. Extension member 110 and constriction member 120 may be selected and/or formed independently of one another.

In some embodiments, as retrieval basket 300 and/or catheter 150 are slid through a patient's body passageway, it will be encouraged to do so in the longitudinal direction extending by the walls of the passageway. Orienting the rim plane and/or basket rim 330 transverse to this longitudinal direction facilitates ensnaring or engaging an foreign body 500 by retrieval basket 300, because an expanded opening 340 (see FIG. 2) defined by basket rim 330 will face and/or be oriented normal to foreign body 500. This may limit or reduce the amount of maneuvering required to position foreign body 500 within retrieval basket 300. It is understood that different designs, constructions, and/or configurations of basket 300 may be included instead of or in addition to the design, construction, and/or configuration shown in the figures. For example, an alternative design may include a substantially football (or elongate) basket, which may or may not have an open end (which may or may not include a constriction element or cinch, such as basket rim 330).

In some embodiments, such as those shown in FIGS. 1-3, five legs 310 may be included and/or used to at least partially form basket 300. However, it is understood that any number of legs 310 may be included and/or used. For example, more or fewer legs 310 may be used to achieve a desired rim shape of basket rim 330 (e.g., four may be used for a substantially square or rectangular basket rim 330, or eight may be used for a substantially octagonal basket rim 330, etc.). The number and/or shape of legs 310 may vary between embodiments for any of a variety of purposes, including, but not limited to, forming a certain basket rim 330 shape and/or achieving a certain outward spring force for biasing basket rim 330 toward expanded position 340. In some embodiments, legs 310 may have gripping and/or holding mechanisms, for example, at or near distal end 316. For example, distal ends 316 may be slightly bent inwardly, toward the center of basket rim 330, and/or include inwardly projecting members, to enhance the capability of basket 300 to grip, hold, and/or secure foreign body 500 therein (e.g., by digging into foreign body 500 when basket 300 and/or basket rim 330 is in the constricted position). Legs 310 may be formed of any of a variety of materials, including, but not limited to any of a variety of metals or alloys such as stainless steel or nitinol, plastic, or any other material, or any combination thereof. It is understood that, in some embodiments, the materials may be selected for one or more purposes such as, for example, to resist buckling upon actuation of the device, to have a spring-like temper so that legs 310 may have resilience to repeated openings and closings, be non-ferrous for MRI compatibility, and/or be amenable to working in an acidic environment. The basket and/or individual basket legs can be formed using methods including but not limited to a laser cut tube, flattened or formed wires, die stamping, coining, or any combination of these.

Basket rim 330 may be connected to, in communication with, and/or integral with constriction member or constriction wire 120. Constriction wire 120 may extend through catheter 150, through coupling 250, and/or into handle 200.

Constriction wire 120 may extend out of handle 200 and/or have a wire hold 125 that is accessible so that an operator may pull and/or move wire hold 125 to a first or constriction position to, for example, shorten the length of constriction wire 120 available to form basket rim 330 and thereby constrict or cause corresponding constriction of basket rim 330 and/or retrieval basket 300 to, for example, form constricted opening 350 (see FIG. 3). Such constriction of basket rim 330 may be used to grip, grab, and/or secure foreign body 500 that is at least partially within retrieval basket 300. This constriction of basket rim 330 may also be used to cut, shear, resect, and/or separate foreign body (e.g., a polyp) for easier removal, resection, and/or extraction. In some embodiments, legs 310 may be bent, spring-like, and/or outwardly biased so that when wire hold 125 and/or constriction wire 120 are released, the legs are inclined to move basket rim 330 and/or basket 300 toward a second or expanded position (see FIG. 2). In such embodiments, basket 300 may automatically positioned and/or approach the expanded position (e.g., if the legs 310 are outwardly biased to form expanded opening 340 that may be larger than the passageway through which it is being inserted, the walls of the passageway may limit the size of expanded opening 340 formed by basket rim 330 to be smaller than a fully open or expanded position).

Figure 4:
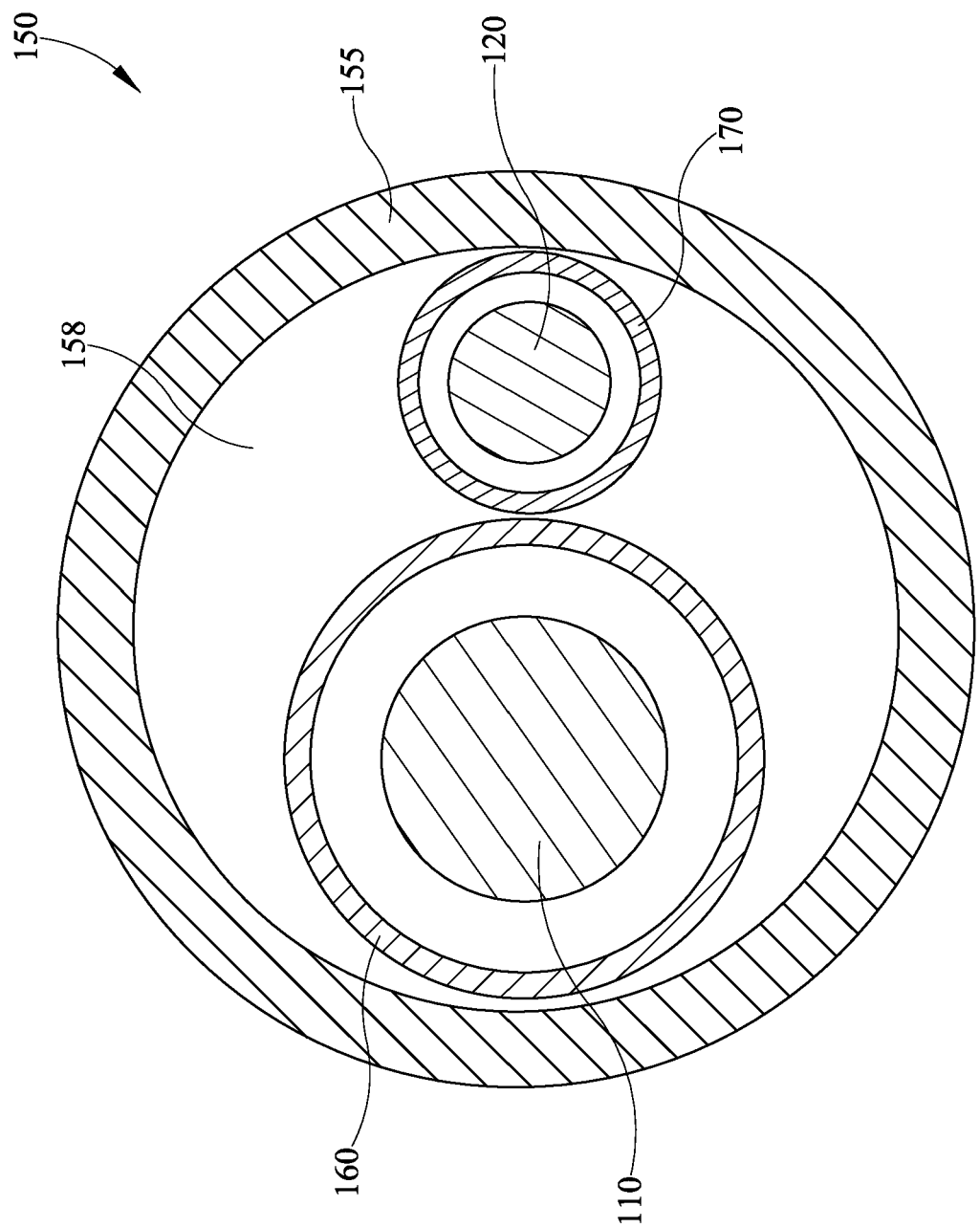
FIG. 4 is a cross-section view of the catheter of FIG. 1 taken along line 4-4.

Referring now to FIG. 4, a cross-section view of catheter 150, taken along line 4-4 shown in FIG. 1, is illustrated. Catheter 150 may include an outer wall or sheath 155 that may substantially define the perimeter of catheter 150 and/or a catheter core 158, which may be hollow or solid, or any combination thereof. A first or cable lumen 160 may be included and, if so, may house or form channel through which extension member 110 may slide. A second or wire lumen 170 may be included and, if so, may house or form a channel through which constriction wire 120 may slide. In some embodiments, use of a separate cable lumen 160 for extension member 110 and wire lumen 170 for constriction wire 120 may allow keeping extension member 110 and constriction wire 120 from contacting one another, from interfering with another, and/or to keep from becoming tangled, which could possibly happen otherwise during the sliding, bending, and/or twisting motions that may accompany the operation of medical retrieval device 100.

It is understood that additional features may be used instead of, or in addition to, those described herein. For example, medical retrieval device 100 may include, in addition to basket 300 and/or constriction wire 120, any of a variety of other features, including, but not limited to, forceps, lights or lighting, camera(s) or optical devices, sensors, or any other feature or any combination thereof. In some embodiments, medical retrieval device 100, or any component or feature thereof, may be used over guidewire and/or medical retrieval device 100 may be modified or altered to accommodate use of a guidewire. Continuing this example, one or more additional lumens (e.g., in addition to cable lumen 160 and wire lumen 170) may be added to facilitate use of any or all of the additional (or substitute) features. Forceps, for example, may be used and/or may extend outwardly from catheter 150 at or near basket end 154. Such forceps, if included, may be controlled by a cable or wire, which may be operatively connected to handle 200, such as described above. However, it is understood that forceps are optional and, if included, may be placed at any of a variety of locations and controlled in any of a variety of ways. It is further understood that, if additional or other features are included, an associated lumen may be included therewith, a lumen or lumens may be shared, or any feature may be included and/or used without a lumen.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms. The indefinite articles "a" and "an," as used herein in the specification and in the claims, unless clearly indicated to the contrary, should be understood to mean "at least one." The phrase "and/or," as used herein in the specification and in the claims, should be understood to mean "either or both" of the elements so conjoined, i.e., elements that are conjunctively present in some cases and disjunctively present in other cases.

Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

"Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing description of several methods and embodiments have been presented for purposes of illustration. It is not intended to be exhaustive or to limit the precise steps and/or forms disclosed, and obviously many modifications and variations are possible in light of the above teaching. It is intended that the scope and all equivalents be defined by the claims appended hereto.

What is claimed is:

1. A method of removing an object from within a body of a patient, comprising the steps of:
    extending a retrieval basket towards said object, wherein said retrieval basket includes a plurality of legs and a constriction member, wherein each leg of said plurality of legs includes a distal end, wherein said constriction member forms a basket rim engaging each said distal end of said plurality of legs;
    actuating said constriction member; and
    constricting said basket rim onto said object by slidably engaging said constriction member with each one of said distal ends before ending at a termination end of said constriction member fixedly secured to at least one of said distal ends previously slideably engaged.

2. The method of claim 1 wherein the step of constricting includes tightening said constriction member in a single circumferential direction about said basket rim.

3. The method of claim 1 further comprising the step of retracting said basket rim and said object into a sheath.

4. The method of claim 3 further comprising the step of constricting said sheath.

5. The method of claim 1 further comprising the step of forming said basket rim in a plane substantially transverse to the direction of extending said retrieval basket towards said object.

6. The method of claim 1 further comprising the step of rotating said retrieval basket.

7. The method of claim 1 further comprising the step of expanding said basket rim.

8. The method of claim 1 wherein said constriction member extends substantially 360 degrees about said basket rim.

9. The method of claim 1 further comprising a handle coupled to said retrieval basket via an extension member and said constriction member, said extension member and said constriction member slidably engaged with at least one lumen of a catheter, said catheter and said at least one lumen extending longitudinally away from said handle toward said retrieval basket.

10. A method of removing an object from within a body of a patient, comprising the steps of:
    inserting a medical retrieval device into said body of said patient, wherein said medical retrieval device comprises:
        a plurality of legs in longitudinal translational communication with an extension member, each leg of said plurality of legs in radial translatable communication with a basket rim;
        each leg of said plurality of legs having a proximal end and a distal end, each said proximal end connected to said extension member, wherein said extension member is slidably engageable with a catheter; each said distal end extended longitudinally away from each said proximal end;
        a constriction member forming said basket rim engaging each said distal end of said plurality of legs, each said distal end biased radially outwardly from each said proximal end biasing said basket rim toward an expanded position;
    actuating said constriction member causes constriction of said basket rim from said expanded position to a constricted position, wherein when in said constricted position said basket rim is capable of constricting onto said object, and said constriction of said basket rim capable of overcoming said radially outwardly bias of each said distal end of said plurality of legs, and wherein said constriction member extends substantially 360 degrees about said basket rim thereby twice engaging at least one said distal end of said leg; and
    constricting said constriction member substantially 360 degrees about at least a portion of said object when in said constricted position and tightening said constriction member in a single circumferential direction about said basket rim.

11. The method of claim 10 further comprising the step of retracting said basket rim and said object into a sheath.

12. The method of claim 11 further comprising the step of constricting said sheath.

13. The method of claim 10 further comprising the step of rotating said retrieval basket.

14. The method of claim 10 further comprising the step of expanding said basket rim to said expanded position.

15. The method of claim 10 further comprising the step of engaging said object with each said distal end of said plurality of legs.

16. The method of claim 10 wherein said constriction member is both fixedly secured to and slidably engaged to at least one of said distal ends of said plurality of said plurality of legs.

17. A method of removing an object from within a body of a patient, comprising the steps of:
- inserting a medical retrieval device into said body of said patient, wherein said medical retrieval device comprises:
  - a plurality of legs in longitudinal translational communication with an extension member, each leg of said plurality of legs in radial translatable communication with a basket rim;
  - each leg of said plurality of legs having a proximal end and a distal end, each said proximal end connected to said extension member, wherein said extension member is slidably engageable with a catheter; each said distal end extended longitudinally away from each said proximal end;
  - a constriction member forming said basket rim engaging each said distal end of said plurality of legs, each said distal end biased radially outwardly from each said proximal end biasing said basket rim toward an expanded position, and wherein said constriction member is both fixedly secured to and slidably engaged to at least one of said distal ends of said plurality of said plurality of legs:
- actuating said constriction member causes constriction of said basket rim from said expanded position to a constricted position, wherein when in said constricted position said basket rim is capable of constricting onto said object, and said constriction of said basket rim capable of overcoming said radially outwardly bias of each said distal end of said plurality of legs, and wherein said constriction member extends substantially 360 degrees about said basket rim thereby twice engaging at least one said distal end of said leg; and
- constricting said constriction member substantially 360 degrees about at least a portion of said object when in said constricted position.

18. The method of claim 17 further comprising the step of retracting said basket rim and said object into a sheath.

19. The method of claim 18 further comprising the step of constricting said sheath.

20. The method of claim 17 further comprising the step of rotating said retrieval basket.

21. The method of claim 17 further comprising the step of expanding said basket rim to said expanded position.

22. The method of claim 17 further comprising the step of engaging said object with each said distal end of said plurality of legs.

* * * * *